United States Patent
Kawachi et al.

(10) Patent No.: US 9,440,901 B2
(45) Date of Patent: Sep. 13, 2016

(54) METHOD FOR PRODUCING REDUCED COENZYME Q10

(71) Applicant: KANEKA CORPORATION, Osaka-shi (JP)

(72) Inventors: Hideo Kawachi, Takasago (JP); Shiro Kitamura, Osaka (JP); Yasuyoshi Ueda, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 14/397,363

(22) PCT Filed: Apr. 26, 2013

(86) PCT No.: PCT/JP2013/062506
§ 371 (c)(1),
(2) Date: Oct. 27, 2014

(87) PCT Pub. No.: WO2013/162034
PCT Pub. Date: Oct. 31, 2013

(65) Prior Publication Data
US 2015/0284311 A1    Oct. 8, 2015

(30) Foreign Application Priority Data
Apr. 27, 2012   (JP) .................. 2012-103687

(51) Int. Cl.
*C07C 46/10* (2006.01)
*C07C 41/40* (2006.01)

(52) U.S. Cl.
CPC ............... *C07C 46/10* (2013.01); *C07C 41/40* (2013.01); *C07B 2200/13* (2013.01)

(58) Field of Classification Search
CPC .... C07C 46/10; C07C 41/40; C07B 2200/13
See application file for complete search history.

(56) References Cited

U.S. PATENT DOCUMENTS

| | | |
|---|---|---|
| 6,184,255 B1 | 2/2001 | Mae et al. |
| 2004/0197886 A1 | 10/2004 | Ueda et al. |
| 2004/0214301 A1 | 10/2004 | Ueda et al. |
| 2004/0215040 A1 | 10/2004 | Ueda et al. |
| 2005/0008630 A1 | 1/2005 | Ueda et al. |
| 2005/0074860 A1 | 4/2005 | Ueda et al. |
| 2006/0246565 A1* | 11/2006 | Ueda ...................... C07C 41/36  435/183 |

FOREIGN PATENT DOCUMENTS

| | | |
|---|---|---|
| JP | 10-109933 | 4/1998 |
| JP | 2003 89669 | 3/2003 |
| JP | 2006-8681 | 1/2006 |
| JP | 2006 513274 | 4/2006 |
| JP | 2009 46495 | 3/2009 |
| WO | 03/006408 | 1/2003 |
| WO | 03 006411 | 1/2003 |
| WO | WO 2005/033054 A1 | 4/2005 |

OTHER PUBLICATIONS

Ulrich, Kirk Othmer Encyclopedia of Chemical Technology, vol. 8, Crystallization, 2002, John Wiley & Sons, Inc., New York, pp. 95-147.*
International Search Report Issued Jul. 16, 2013 in PCT/JP13/062506 Filed Apr. 26, 2013.

* cited by examiner

*Primary Examiner* — Paul A Zucker
(74) *Attorney, Agent, or Firm* — Oblon, McClelland, Maier & Neustadt, L.L.P.

(57) ABSTRACT

Provided is a production method of Form I crystal of reduced coenzyme Q10 or a crystalline solid thereof, which is substantially free of Form II crystal, including a step of holding a solution containing reduced coenzyme Q10 at a temperature exceeding 47° C. for at least 60 minutes, and a step of crystallization thereafter.

21 Claims, No Drawings

METHOD FOR PRODUCING REDUCED COENZYME Q10

TECHNICAL FIELD

The present invention relates to a production method of reduced coenzyme Q10. More particularly, the present invention relates to a production method of Form I crystal of reduced coenzyme Q10 or a crystalline solid thereof, which is substantially free of Form II crystal.

BACKGROUND ART

Coenzyme Q is an essential component widely distributed in living organisms from bacterium to a mammal, and is known as a constituent component of an electron transport system of mitochondria in the cells of living organisms. It is known that coenzyme Q performs a function of a messenger component in an electron transport system by repeating oxidation and reduction in mitochondria, and that reduced coenzyme Q has an antioxidant action. In human, coenzyme Q10, which is coenzyme Q having a side chain with 10 repeated structures, is the main component, and about 40-90% is generally present as reduced type in the living body. The physiological action of coenzyme Q includes activation of energy production by mitochondria activating action, activation of cardiac function, cellular membrane stabilizing effect, cell protection effect by antioxidant action and the like.

Coenzyme Q10 currently produced and sold is mostly oxidized. In recent years, reduced coenzyme Q10 that shows high oral absorbability as compared to oxidized coenzyme Q10 has also been released in the market and is increasingly used.

A general method for obtaining reduced coenzyme Q10 has already been disclosed (patent document 1). As for a method for obtaining reduced coenzyme Q10 as crystals, some methods are known. For example, a method including crystallizing reduced coenzyme Q10 in an alcohol solution and/or a ketone solution to produce crystals (patent document 2), a method including crystallizing reduced coenzyme Q10 in a solvent containing citric acids and/or ascorbic acid (patent document 3), a method including crystallizing reduced coenzyme Q10 by adding a high concentration liquid phase thereof into a poor solvent (patent document 4) and the like have been reported.

In addition, it has been disclosed that a crystal superior in stability and having an X-ray diffraction pattern different from that of general reduced coenzyme Q10 crystal can be obtained by dissolving reduced coenzyme Q10 in fats and oils and cooling same (patent document 5).

It has been reported that, generally, whether organic compound or inorganic compound, many compounds have plural crystal forms having different crystal structures, and this is called crystal polymorph. Such plural crystal forms present in crystal polymorph show not only different patterns in analyses such as X-ray diffraction, infrared spectroscopic analysis and the like, but also different properties such as melting point, solubility and the like. When the substance has a physiological activity of pharmaceutical products, functional foods and the like, the substance sometimes shows different bioavailability. It is commonly known that crystal polymorph should be strictly controlled by, for example, setting the judgment criteria for the content of each crystal form in a pharmaceutical product, and the like, when such difference in the crystallinity affects the function of a preparation, bioavailability or stability (non-patent document 1).

On the other hand, it is also true that the crystal polymorphism has not been elucidated sufficiently. While serious phenomena have been reported wherein the dosage form of a pharmaceutical product already placed in the market needs to be changed, or the development strategy of a pharmaceutical product under development needs to be changed or cancelled, because a new crystal form suddenly emerges one day and a crystal form present until then is no longer obtainable, what causes such phenomena has not been clarified to date (non-patent documents 2, 3).

DOCUMENT LIST

Patent Documents patent document 1: JP-A-10-109933
patent document 2: WO 2003/006409
patent document 3: JP-A-2006-008681
patent document 4: JP-A-2003-089669
patent document 5: WO 2005/033054

Non-Patent Documents non-patent document 1: Pharmaceutical Affairs Bureau Notification No. 568 "shin-iyakuhin no kikaku oyobi shiken houhou no settei ni tsuite" 3.3
non-patent document 2: Masakuni Matsuoka ed. "wakariyasui kessyo takei" (Society of Separation Process Engineers) P. 4
non-patent document 3: J. D. Dunitz and J. Bernstein, "Disappearing Polymorphs" Acc. Chem. Res., 28, 193-200 (1995)

DISCLOSURE OF THE INVENTION

Problems to be Solved by the Invention

There is no clear report on the crystal polymorph of both the oxidized and reduced forms of coenzyme Q10, and the crystal polymorph was considered to be nonexistent. Surprisingly, however, the present inventors have just recently found that reduced coenzyme Q10 shows crystal polymorphism. The newly-emerged crystal form was confirmed to show lower solubility and a higher melting point than conventional reduced coenzyme Q10 crystals (hereinafter this crystal is referred to as Form I). Therefore, the newly-found crystal form (hereinafter this crystal is referred to as Form II) is a stable form, and conventional reduced coenzyme Q10 crystal was clarified to be a metastable form relatively unstable as compared to the newly-found crystal form.

Ever since Form II crystal of reduced coenzyme Q10 was found, a problem which was absent until then was suddenly developed in the production of reduced coenzyme Q10. To be precise, conventionally-absent Form II crystal came to be found from time to time in the reduced coenzyme Q10 crystal obtained by a conventional production method. The present inventors newly developed an analysis method for detection of Form II crystal and observed the situation. As a result, it was found that the amount of the Form II crystal in the crystal is sometimes a trace amount present in conventional Form I crystal and sometimes the obtained crystal is mostly Form II crystal. When Form II crystal is contained in the produced reduced coenzyme Q10 crystal, Form I crystal may be obtained by dissolving the crystal and performing the crystallization again. In this case, however, ensured production of Form I crystal alone is not guaranteed, and this method is not an efficient method. As described above, crystal polymorph should be strictly controlled in pharmaceutical products, functional foods and the like, and the development of a method for completely controlling the crystal polymorph of reduced coenzyme Q10 is also demanded. Moreover, since Form II crystal is not easily dissolved in a solvent and the like as compared to Form I crystal, the presence of Form II crystal is not preferable depending on the use, and a method of certainly obtaining Form I crystal alone has become a new problem.

Means of Solving the Problems

The present inventors have conducted intensive studies in an attempt to solve the aforementioned completely new problem of control of crystal polymorph, which is conventionally not present, and found a method of certainly obtaining Form I crystal alone in the production of reduced coenzyme Q10 crystal, which resulted in the completion of the present invention.

That is, the present invention is a method of producing Form I crystal of reduced coenzyme Q10 or a crystalline solid thereof, which is substantially free of Form II crystal, comprising a step of holding a solution containing reduced coenzyme Q10 at a temperature exceeding 47° C. for at least 60 minutes, and a step of crystallization thereafter.

Accordingly, the present invention provides the following.

[1] A method of producing Form I crystal of reduced coenzyme Q10 or a crystalline solid thereof, which is substantially free of Form II crystal, comprising a step of holding a solution containing reduced coenzyme Q10 at a temperature exceeding 47° C. for at least 60 minutes, and a step of crystallization thereafter.
[2] The production method of [1], wherein the solution containing reduced coenzyme Q10 is a solution wherein reduced coenzyme Q10 is dissolved in at least one solvent selected from the group consisting of hydrocarbons, fatty acid esters, ethers, alcohols, ketones, nitrogen compounds, sulfur compounds and water.
[3] The production method of [1] or [2], wherein the crystallization step is cooling crystallization, poor solvent crystallization, or a combination of cooling crystallization and other crystallization method.
[4] The production method of any one of [1]-[3], wherein the crystallization step includes a step of adding Form I crystal of reduced coenzyme Q10 or a crystalline solid thereof.
[5] The production method of [4], wherein the amount of Form I crystal or a crystalline solid thereof to be added is 0.001-10 wt % relative to the amount of reduced coenzyme Q10 dissolved in the solution.
[6] The production method of any one of [1]-[5], wherein the average temperature variation during holding of the solution containing reduced coenzyme Q10 at a temperature exceeding 47° C. is less than 3° C./h.
[7] The production method of any one of [1]-[6], wherein the crystallization step is performed at less than 25° C.
[8] The production method of any one of [1]-[7], wherein the crystallization step requires less than 24 hours.
[9] The production method of any one of [1]-[8], wherein the crystallization step is performed under a forced flow that renders the mixing time (θ) not more than 5 minutes.
[10] The production method of [9], wherein the forced flow is produced by rotation of mixing blades.
[11] The production method of [10], wherein the mixing blade has a mixing blade diameter/tank diameter (d/D) ratio of not less than 0.85, or is used together with a baffle.
[12] The production method of any one of [1]-[11], wherein the step of holding at a temperature exceeding 47° C. and the crystallization step are performed in an industrial scale.

Effect of the Invention

According to the present invention, the crystal polymorph of reduced coenzyme Q10 is certainly controlled, and Form I crystal of reduced coenzyme Q10, which is substantially free of Form II crystal, can be efficiently produced in an industrial scale.

DESCRIPTION OF EMBODIMENTS

The present invention is explained in detail in the following.

In the present specification, the "reduced coenzyme Q10" may contain oxidized coenzyme Q10 in a part thereof as long as reduced coenzyme Q10 is the main component. The main component here means that it is contained in a proportion of, for example, not less than 50 wt %, generally not less than 60 wt %, preferably not less than 70 wt %, more preferably not less than 80 wt %, further preferably not less than 90 wt %, particularly preferably not less than 95 wt %, especially not less than 98 wt %.

In the present specification, moreover, the "crystalline solid" means a solid containing an amorphous component without a crystal structure, together with a part having a crystal structure.

The production method of Form I crystal of reduced coenzyme Q10 and a crystalline solid thereof of the present invention characteristically has (1) a step of holding a solution containing reduced coenzyme Q10 at a temperature exceeding 47° C. for at least 60 minutes, and (2) a step of crystallization thereafter.

First, (1) a step of holding a solution containing reduced coenzyme Q10 at a temperature exceeding 47° C. for at least 60 minutes (hereinafter to be referred to as "holding step") is explained.

While the temperature condition in the holding step is not particularly limited as long as it is a temperature exceeding 47° C., a temperature exceeding 50° C. is preferable, not less than 52° C. is more preferable, not less than 55° C. is further preferable, and not less than 60° C. is particularly preferable.

While the upper limit of the temperature conditions is generally the boiling point of the solvent to be used, this does not apply as long as the treatment can be performed under pressurization. In view of such aspect, the temperature conditions are not particularly limited. It is generally not more than 180° C., preferably not more than 150° C., more preferably not more than 120° C., further preferably not more than 100° C., particularly preferably less than 78° C., and especially preferably not more than 75° C.

While the holding time is not particularly limited as long as it is not less than 60 minutes, it is preferably not less than 90 minutes, and more preferably not less than 120 min.

While the upper limit of the holding time is not particularly limited, it is generally not more than 72 hours, preferably not more than 48 hours, more preferably not more than 24 hours, and particularly preferably not more than 12 hours.

The holding of temperature in the present invention is not only holding at a given temperature exceeding 47° C. for a given time, but also that accompanying an increase or decrease of the temperature as long as it is within the range exceeding 47° C. When the temperature accompanies an increase or decrease, the range of variation of the temperature is preferably controlled to some extent and, for example, holding within a given temperature width range is also one of the preferable embodiments of the present invention. The temperature width in this case is not particularly limited as long as it can be controlled in actual production. For example, the range including the given temperature is about 10° C., preferably about 8° C., more preferably about 6° C., further preferably about 4° C., particularly preferably about 2° C.

On the other hand, the temperature variation accompanying an increase or decrease of the temperature in the holding step is not particularly limited. A mild temperature variation is preferable. To be specific, the average temperature variation is preferably less than 3° C./h, more preferably not more than 2.5° C./h, further preferably not more than 2° C./h, and particularly preferably not more than 1° C./h. The average temperature variation here is calculated as "temperature change (° C.)/holding time (h)" during holding at a temperature exceeding 47° C. for a given time (at least 60 minutes). In the holding step in the production method of the present invention, a solution containing reduced coenzyme Q10 is preferably held at a given temperature exceeding 47° C. for a given time.

In the holding step, a method of holding a solution containing reduced coenzyme Q10 at a temperature exceeding 47° C. for a given time is not particularly limited. A solution containing reduced coenzyme Q10 is heated to a given temperature exceeding 47° C., and maintained for at least 60 min at a temperature exceeding 47° C. by controlling the temperature, holding the temperature and the like. In the holding step, a solution containing reduced coenzyme Q10 may be in a mixed state by stirring, solution circulation and the like, or in a standstill state, with preference given to a mixed state.

The solution containing reduced coenzyme Q10 to be subjected to the holding step is not particularly limited as long as it contains reduced coenzyme Q10. It may be in a uniform solution state in which reduced coenzyme Q10 is dissolved or in a slurry state wherein reduced coenzyme Q10 partially remains undissolved, with preference given to a uniform solution state.

Furthermore, it is preferable to use, as a solution containing reduced coenzyme Q10, a solution wherein reduced coenzyme Q10 is dissolved in at least one solvent selected from the group consisting of hydrocarbons, fatty acid esters, ethers, alcohols, ketones, nitrogen compounds, sulfur compounds and water.

The reduced coenzyme Q10 to be dissolved here may be a crystal or an amorphous crystal, and may have any crystal polymorph. Moreover, reduced coenzyme Q10 may have impurity or may be unpurified or crudely purified, since the purity thereof can be increased in the crystallization step to be mentioned later. Furthermore, an extract of reduced coenzyme Q10, which is obtained by a conventionally known method or a reaction mixture containing reduced coenzyme Q10 obtained from oxidized coenzyme Q10 by a known reduction method can also be used directly, or after purification and/or solvent-substitution as necessary, as a solution containing reduced coenzyme Q10.

While the above-mentioned hydrocarbons are not particularly limited, for example, aliphatic hydrocarbon, aromatic hydrocarbon, halogenated hydrocarbon and the like can be mentioned.

While aliphatic hydrocarbon may be cyclic or acyclic, saturated or unsaturated and is not particularly limited, aliphatic hydrocarbon having 3 to 20 carbon atoms, preferably 5 to 12 carbon atoms, can be generally used. Specific examples of the aliphatic hydrocarbon include propane, butane, isobutane, pentane, 2-methylbutane, cyclopentane, 2-pentene, hexane, 2-methylpentane, 2,2-dimethylbutane, 2,3-dimethylbutane, methyl cyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane, dodecane and the like.

While the aromatic hydrocarbon is not particularly limited, normally, aromatic hydrocarbon having 6 to 20 carbon atoms, preferably 6 to 12 carbon atoms, more preferably 7 to 10 carbon atoms, is preferably used. Specific examples of the aromatic hydrocarbon include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene and the like.

The halogenated hydrocarbon may be cyclic or acyclic, saturated or unsaturated, and is not particularly limited. Acyclic one is preferably used. Chlorinated hydrocarbon and fluorinated hydrocarbon are more preferable, and chlorinated hydrocarbon is particularly further preferable.

In addition, a halogenated hydrocarbon having 1 to 6 carbon atoms, preferably to 4 carbon atoms, more preferably 1 or 2 carbon atoms, is used. Specific examples of the halogenated hydrocarbon include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane and the like.

While the above-mentioned fatty acid esters are not particularly limited, for example, propionic acid ester, acetic acid ester, formic acid ester and the like can be mentioned. Acetic acid ester or formic acid ester is preferable, and acetic acid ester is more preferable.

While the ester group is not particularly limited, alkylester having 1-8 carbon atoms, aralkylester having 1-8 carbon atoms and the like can be mentioned. Preferred is alkyl ester having 1 to 6 carbon atoms, and more preferred is alkyl ester having 1 to 4 carbon atoms.

Examples of propionic acid ester include methyl propionate, ethyl propionate, butyl propionate and isopentyl propionate.

Examples of the acetic acid ester include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate and the like.

Examples of formic acid ester include methyl formate, ethyl formate, propyl formate, isopropyl formate, butyl formate, isobutyl formate, sec-butyl formate, pentyl formate and the like.

The above-mentioned ethers may be cyclic or acyclic, or saturated or unsaturated, and are not particularly limited. Saturated ones are preferably used. Generally, an ester having 3-20 carbon atoms, preferably 4-12 carbon atoms, more preferably 4-8 carbon atoms, is used.

Specific examples of the ethers include diethyl ether, methyl tert-butyl ether, dipropyl ether, diisopropyl ether, dibutyl ether, dihexyl ether, ethylvinyl ether, butylvinyl ether, anisole, phenetole, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether and the like.

The above-mentioned alcohols may be cyclic or acyclic, or saturated or unsaturated, and are not particularly limited. Saturated ones are preferably used. For example, monohydric alcohol having 1-20 carbon atoms, preferably 1-12 carbon atoms, more preferably 1-6 carbon atoms, further preferably 1-5 carbon atoms, particularly preferably 1-4 carbon atoms, especially preferably 1-3 carbon atoms, can be mentioned. Most preferred is monohydric alcohol having 2-3 carbon atoms. In addition, divalent alcohol having 2-5 carbon atoms, preferably 2-3 carbon atoms, trivalent alcohol having 3 carbon atoms, and the like are also used preferably. Among the above, monohydric alcohol having 1-5 carbon atoms has high compatibility with water, and is preferably used as a mixed solvent with water.

Examples of the monohydric alcohol include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol and the like.

Examples of the divalent alcohol include 1,2-ethanediol, 1,2-propanediol, 1,3-propanediol, 1,2-butanediol, 1,3-butanediol, 1,4-butanediol, 2,3-butanediol, 1,5-pentanediol and the like.

Examples of the trivalent alcohol include glycerol and the like.

The above-mentioned ketones are not particularly limited, and those having 3-6 carbon atoms are preferably. Specific examples include acetone, methyl ethyl ketone, methyl butyl ketone, methyl isobutyl ketone and the like.

As the above-mentioned nitrogen compounds, nitriles can be used. The nitriles may be cyclic or acyclic, or saturated or unsaturated, and are not particularly limited. Saturated ones are preferably used. Normally, nitrile having 2 to 20 carbon atoms, preferably 2 to 12 carbon atoms, more preferably 2 to 8 carbon atoms, is preferably used.

Specific examples of the nitriles include acetonitrile, propionitrile, malononitrile, butyronitrile, isobutyronitrile, succinonitrile, valeronitrile, glutaronitrile, hexanenitrile, heptyl cyanide, octyl cyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyanide, cyclopropanecarbonitrile, cyclohexanecarbonitrile, cycloheptanecarbonitrile, phenylcyclohexanecarbonitrile, tolylcyclohexanecarbonitrile and the like.

Examples of the nitrogen compounds other than the aforementioned nitriles include nitromethane, triethylamine, pyridine, formamide, N-methylformamide, N,N-dimethylformamide, N,N-dimethylacetamide, N-methylpyrrolidone and the like.

Examples of the above-mentioned sulfur compounds include dimethyl sulfoxide, sulfolane and the like.

Among the above-mentioned solvents, hydrocarbons, nitriles, alcohols and ketones are preferable, alcohols or ketones are more preferable, and alcohols are particularly preferable.

In the present invention, as a solvent for dissolving reduced coenzyme Q10, those exemplified above may be used alone. To improve the conditions affecting the crystallization conditions such as solubility of reduced coenzyme Q10, crystallization concentration, yield, slurry property, crystallinity and the like, according to the property of each solvent, two or more kinds can also be used by mixing at a preferable ratio.

The concentration of reduced coenzyme Q10 in a solution containing reduced coenzyme Q10 to be subjected to the holding step and the crystallization step thereafter is preferably set to such a concentration that achieves complete dissolution of reduced coenzyme Q10 at the holding temperature.

The specific concentration is within the range not exceeding of the solubility at the maintenance temperature of the solvent to be used. The upper limit is preferably not more than 50 wt %, more preferably not more than 40 wt %, particularly preferably not more than 30 wt %. From the aspect of production efficiency, the concentration of reduced coenzyme Q10 in the solution is preferably adjusted to a concentration as high as possible, which is, for example, preferably not less than 1 wt %, more preferably not less than 3 wt %, and particularly preferably not less than 5 wt %.

In the production method of the present invention, the step (2) of crystallization of reduced coenzyme Q10 (hereinafter to be referred to as "crystallization step") is performed after the holding step of (1). Here, the crystallization step may be performed continuously from the holding step, or performed after some step following the holding step, for example, purification, solvent substitution and the like. In addition, the thermal history up to the crystallization step after the holding step is not particularly limited. However, (2) crystallization step is preferably performed continuously from (1) holding step.

In a general production method of reduced coenzyme Q10, the concentration of reduced coenzyme Q10 and the kind of the crystallization solvent in the crystallization step greatly influence the crystallization ratio and the purity of the obtained crystal of reduced coenzyme Q10. Therefore, generally, when crystallization is performed continuously from a reduction reaction, the concentration and conditions are frequently controlled to be suitable for crystallization by adding a solvent or performing concentration/solvent substitution and the like after completion of the reduction reaction. In the production method of the present invention, when the reaction solution of reduced coenzyme Q10, which is obtained by the reduction reaction, is subjected to (1) holding step, it is preferable to previously control the conditions of reduced coenzyme Q10 to those suitable for subsequent (2) crystallization step, and then perform the holding step. For example, it is preferable to add a solvent to the reaction solution of reduced coenzyme Q10, which is obtained by the reduction reaction, and then perform (1) holding step, and continuously perform (2) crystallization step.

In addition, a production method of reduced coenzyme Q10, including a step of dissolving reduced coenzyme Q10 in a solvent, (1) holding step, and (2) crystallization step, particularly, a production method including continuously performing the aforementioned three steps can be preferably mentioned.

(2) Crystallization Step is Explained Below.

In the present invention, the method for crystallizing reduced coenzyme Q10 to be performed in the crystallization step is not particularly limited; however, cooling crystallization, poor solvent crystallization or a combination of cooling crystallization and other crystallization method is preferable. Cooling crystallization is a method of crystallizing a solute by cooling a solution to decrease solubility, and poor solvent crystallization is a method of crystallizing a solute by mixing a solution and a poor solvent to decrease solubility. As used herein, the poor solvent refers to a solvent that scarcely dissolves reduced coenzyme Q10 or does not dissolve reduced coenzyme Q10 at all. The poor solvent and a solution containing reduced coenzyme Q10 are preferably dissolved in each other.

As a method of mixing with a poor solvent, a poor solvent may be added to a solution or a solution may be added to a poor solvent. As other crystallization method to be combined with cooling crystallization, the aforementioned poor solvent crystallization as well as, for example, concentration crystallization that precipitates a crystal by concentrating a solution, and the like can be mentioned.

In the production method of the present invention, a preferable crystallization method is cooling crystallization or poor solvent crystallization, and a particularly preferable crystallization method is cooling crystallization.

In crystallization, a seed crystal is preferably added for smooth nucleation and crystal growth. Preferred as the seed crystal to be added is Form I crystal of reduced coenzyme Q10 or a crystalline solid containing Form I crystal. The amount of the seed crystal to be added is preferably 0.001-10 wt %, more preferably 0.003-5 wt %, particularly preferably 0.005-1 wt %, relative to the amount of reduced coenzyme Q10 dissolved in a solution.

In the crystallization step, a crystal of reduced coenzyme Q10 is preferably precipitated at a temperature less than 25° C. In this case, crystallization may be performed at a given temperature less than 25° C. Particularly, in cooling crystallization, the temperature may become less than 25° C. in the last stage of the cooling step. When a crystal is precipitated at a temperature of not less than 25° C., the yield of the crystal may decrease or a long time may be required to achieve the object yield. From the aspect of productivity, the time necessary for crystallization operation is preferably less than 24 hours, particularly in an industrial scale operation.

Crystallization is preferably performed under a forced flow, to suppress formation of a topical high supersaturation state and perform nucleation and crystal growth smoothly, or to provide high quality. The forced flow is preferably applied to render the mixing time ($\theta$) not more than 5 minutes.

The mixing time ($\theta$) here refers to the time necessary for two or more substances to be mixed spacially uniformly, and used as an index for evaluating the mixing state in the system. The mixing time ($\theta$) relates to the properties of the apparatus such as the size and shape of mixing blade, the presence or absence of baffle and the like, as well as the property of the solution to be mixed, stirring rotation number and the like, and they are shown by a correlation curve of mixing time ($\theta$) and Reynolds number (Re). The correlation curve of mixing time ($\theta$) and Reynolds number (Re) can be comprehended by, for example, adding dye, electrolyte solution and the like to a reduced coenzyme Q10 solution or a model solution replacing same in a stirring apparatus, and measuring the time before stabilization of the numerical values by a spectrometer, a turbidimeter, or an electric conductivity meter, or measuring the time before disappearance of color by utilizing an iodine decoloration reaction by sodium thiosulfate. In addition, it can also be simulated by performing a flow analysis.

The above-mentioned forced flow can be performed by, for example, a method using circulation of solution by the rotation of mixing blades, pump and the like, blowing of a gas, and the like. Preferred is a method including rotation of mixing blades. As the mixing blade to be used for the forced flow, a mixing blade having a diameter/tank diameter (inner diameter of stirring tank) (d/D) ratio of not less than 0.85, or a mixing blade to be used with a baffle is preferable. The shape of the mixing blade may be any of the conventionally-known blade shapes, which can be used without particular constraint.

For example, a mixing blade with d/D of not less than 0.85 may be chosen from mixing blades such as anchor blade, wide paddle blade, large lattice blade, three-way sweptback blade and the like, a mixing blade such as flat plate paddle blade, rake paddle blade, turbine wing, propeller blade and the like may be used with a baffle, or these may be used in combination.

The production method of the present invention is also suitable for performing (1) holding step and (2) crystallization step in an industrial scale. In a small laboratory scale production, the temperature of a solution rarely becomes uneven. However, when reduced coenzyme Q10 is produced in an industrial scale, a comparatively long time is sometimes required for the entire solution in an apparatus to reach a desired temperature, even when a thermometer equipped to the apparatus indicates the desired temperature. Since the production method of the present invention characteristically includes a step of holding at a given temperature for not less than 60 minutes, which is easily controlled even in an industrial scale, it can certainly produce reduced coenzyme Q10 substantially free of Form II crystal, irrespective of the scale of practice.

The industrial scale here refers to, for example, production of not less than 5 kg, preferably not less than 10 kg, more preferably not less than 20 kg, of reduced coenzyme Q10 per 24 hr. In this case, as long as the above-mentioned productivity is satisfied, it may be batch production or continuous production.

Whether or not the crystal of reduced coenzyme Q10 or a crystalline solid thereof contains Form II crystal, and the content ratio thereof can be determined by, for example, measuring with a differential scanning calorimeter (DSC).

When measured by DSC at a temperature rise rate of 1° C./min, Form II crystal shows an endothermic peak near 52±2° C. When measured by DSC at temperature rise rate of 1° C./min, Form I crystal shows an endothermic peak near 48±1° C. Therefore, even if Form II crystal is mixed with conventional Form I crystal or a crystalline solid thereof, the presence or absence of the Form II crystal can be clearly determined by the presence or absence of the aforementioned peak.

According to the method of the present invention, a crystal of reduced coenzyme Q10 or a crystalline solid thereof, in which the presence of Form II crystal is not detected when measured by DSC under the aforementioned conditions, i.e., substantially free of Form II crystal, can be certainly obtained.

The crystal of reduced coenzyme Q10 and a crystalline solid thereof of the present invention, which are obtained by the above-mentioned method, are recovered, for example, by a conventionally-known method such as that as described in patent documents 2 and 3, via solid-liquid separation and drying steps. For example, pressure filtration, centrifugal filtration and the like can be used for the solid-liquid separation. In addition, a crystal of reduced coenzyme Q10 and a crystalline solid thereof after drying can also be recovered by pulverizing and classifying (sieving) as necessary.

The above-mentioned holding step, crystallization step, other post-treatment step and the like are preferably performed, for example, under a deoxygenation atmosphere. The deoxygenation atmosphere can be formed by inert gas replacement, reducing pressure, boiling and combining them. At least, inert gas replacement, that is, use of inert gas atmosphere, is preferable. Examples of the above-mentioned inert gas include nitrogen gas, helium gas, argon gas, hydrogen gas, carbon dioxide gas and the like, preferably nitrogen gas.

EXAMPLES

While the present invention is explained in more detail in the following by referring to Examples, the present invention is not limited to those Examples alone.

DSC measurement conditions in Examples and Comparative Examples are as follows.
(DSC Measurement Condition)
apparatus: DSC6220 manufactured by SII nanotechnology
sample container: aluminum pan & cover (SSC000C008)
temperature rise rate: 1° C./rain
sample amount: 5±2 mg Example 1

The inside of a 2 L separable flask (manufactured by borosilicate glass) is substituted with nitrogen, reduced coenzyme Q10 (100 g) and ethanol (1200 g) were charged therein, and the mixture was heated to 60° C. with stirring by mixing blades to give a uniform solution. This solution was continuously held at 60° C. for 2 hr, and cooled to 35° C. over 1 hr, then from 35° C. to 25° C. over 1 hr, and further from 25° C. to 10° C. over 1 hr to give a crystal of reduced coenzyme Q10. The mixing time θ in the above-mentioned heating, maintenance and cooling steps was 10 seconds, which is obtained from the correlation curve of Reynolds number (Re) and the mixing time (θ), which are measured separately by the apparatus by utilizing an iodine decoloration reaction by sodium thiosulfate.

The same experiment was repeated 10 times, the obtained crystals were respectively analyzed by DSC, and the presence ratio of Form I and Form II in the crystals of reduced coenzyme Q10 was examined. The results are shown in Table 1.

Comparative Example 1

The inside of the same apparatus as that of Example 1 was substituted with nitrogen, reduced coenzyme Q10 (100 g) and ethanol (1200 g) were charged therein, and the mixture was heated to 50° C. with stirring by mixing blades under the same conditions as in Example 1 to give a uniform solution. This solution was heated to 50° C., immediately thereafter cooled to 35° C. over 1 hr, continuously cooled from 35° C. to 25° C. over 1 hr, and further from 25° C. to 10° C. over 1 hr to give a crystal of reduced coenzyme Q10.

The same experiment was repeated 10 times, the obtained crystals of reduced coenzyme Q10 were respectively analyzed by DSC, and the presence ratio of Form I and Form II in the crystals was examined. The results are shown in Table 1.

TABLE 1

| | DSC measurement results (Form I/Form II) | |
|---|---|---|
| Run No. | Example 1 | Comparative Example 1 |
| 1 | 100/0 | 100/0 |
| 2 | 100/0 | 15/85 |
| 3 | 100/0 | 100/0 |
| 4 | 100/0 | 100/0 |
| 5 | 100/0 | 4/96 |
| 6 | 100/0 | 6/94 |
| 7 | 100/0 | 100/0 |
| 8 | 100/0 | 100/0 |
| 9 | 100/0 | 100/0 |
| 10 | 100/0 | 100/0 |

Example 2

The inside of a 2000 L crystallization tank (manufactured by SUS304) was substituted with nitrogen, reduced coenzyme Q10 (100 kg) and ethanol (1200 kg) were charged therein, and the mixture was heated to 60° C. with stirring by mixing blades (d/D=0.9) to give a uniform solution. This solution was continuously held at 60° C.±2° C. for 2 hr, and cooled to 35° C. over 1 hr, then from 35° C. to 25° C. over 1 hr, and further from 25° C. to 10° C. over 1 hr to give a crystal of reduced coenzyme Q10. The mixing time θ in the above-mentioned heating, maintenance and cooling steps was 2 minutes, which is obtained from the correlation curve of Reynolds number (Re) and mixing time θ, which are previously prepared separately by adding an aqueous electrolyte solution (aqueous sodium chloride solution) to water, and measuring the time necessary for stabilizing the values of the conductivity meter equipped to the upper and lower parts of the tank.

The same experiment was repeated 10 times, the obtained crystals of reduced coenzyme Q10 were respectively analyzed by DSC. From the results, the presence of Form II crystal was not confirmed and Form I crystal was confirmed to be substantially 100%.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

The present invention is based on JP2012-103687 filed in Japan, the contents of which are encompassed in full herein.

The invention claimed is:
1. A method of producing Form I crystal of reduced coenzyme Q10 or a crystalline solid thereof, comprising:
holding a solution comprising reduced coenzyme Q10 dissolved therein at a temperature of from 55° C. to 75° C. for at least 60 minutes; and crystallizing the reduced coenzyme Q10 to produce a Form I crystal of the reduced coenzyme Q10 or a crystalline solid thereof, which is substantially free of Form II crystal, wherein the crystallizing comprises cooling the solution, and the Form I crystal shows an endothermic peak near 48±1° C. when measured by DSC at temperature rise rate of 1° C./min.

2. The method according to claim 1, wherein the solution includes the reduced coenzyme Q10 dissolved in at least one solvent selected from the group consisting of a hydrocarbon, a fatty acid ester, an ether, an alcohol, a ketone, a nitrogen compound, a sulfur compound and water.

3. The method according to claim 1, wherein the crystallizing comprises performing a poor solvent crystallization in combination with the cooling of the solution.

4. The method according to claim 1, wherein the crystallizing includes adding a Form I crystal of reduced coenzyme Q10 or a crystalline solid thereof.

5. The method according to claim 4, wherein the Form I crystal or the crystalline solid thereof is added in an amount of 0.001-10 wt % relative to an amount of reduced coenzyme Q10 dissolved in the solution.

6. The method according to claim 1, wherein the holding of the solution is performed such that an average temperature variation is less than 3° C./h.

7. The method according to claim 1, wherein the crystallizing is performed at a temperature of less than 25° C.

8. The method according to claim 1, wherein the crystallizing is performed for less than 24 hours.

9. The method according to claim 1, wherein the crystallizing is performed under a forced flow that causes the mixing time, θ, to be not more than 5 minutes.

10. The method according to claim 9, wherein the forced flow is produced by rotating a mixing blade.

11. The method according to claim 10, wherein the mixing blade has a mixing blade diameter/tank diameter ratio, d/D, of not less than 0.85, or is used together with a baffle.

12. The method according to claim 1, wherein the holding and the crystallizing are performed in an industrial scale.

13. The method according to claim 2, wherein the crystallizing comprises performing a poor solvent crystallization in combination with the cooling of the solution.

14. The method according to claim 2, wherein the crystallizing includes adding a Form I crystal of reduced coenzyme Q10 or a crystalline solid thereof.

15. The method according to claim 14, wherein the Form I crystal or the crystalline solid thereof is added in an amount of 0.001-10 wt % relative to an amount of reduced coenzyme Q10 dissolved in the solution.

16. The method according to claim 2, wherein the holding of the solution is performed such that an average temperature variation is less than 3° C./h.

17. The method according to claim 2, wherein the crystallizing is performed at a temperature of less than 25° C.

18. The method according to claim 2, wherein the crystallizing is performed for less than 24 hours.

19. The method according to claim 2, wherein the crystallizing is performed under a forced flow that causes the mixing time, θ, to be not more than 5 minutes.

20. The method according to claim 19, wherein the forced flow is produced by rotating a mixing blade.

21. The method according to claim 1, wherein the holding is performed for not less than 90 minutes.

* * * * *